United States Patent [19]
Kawasaki

[11] Patent Number: 5,218,091
[45] Date of Patent: Jun. 8, 1993

[54] GLYCOLYTIC PROMOTERS FOR REGULATED PROTEIN EXPRESSION: PROTEASE INHIBITOR

[75] Inventor: Glenn H. Kawasaki, Seattle, Wash.

[73] Assignee: ZymoGenetics, Inc., Seattle, Wash.

[21] Appl. No.: 895,257

[22] Filed: Jun. 8, 1992

Related U.S. Application Data

[60] Continuation of Ser. No. 387,366, Jul. 26, 1989, abandoned, which is a continuation of Ser. No. 868,423, May 29, 1986, abandoned, which is a division of Ser. No. 408,099, Aug. 13, 1982, Pat. No. 4,599,311.

[51] Int. Cl.$^5$ .............................. C07K 13/00
[52] U.S. Cl. ............................ 530/350; 435/172.3; 435/320.1; 435/69.1; 435/256; 435/254; 435/255; 930/250; 935/11; 530/380
[58] Field of Search ............. 530/350, 380; 435/172.3, 320.1, 69.1, 256, 255, 254; 930/250; 935/11

[56] References Cited

U.S. PATENT DOCUMENTS
4,732,973  3/1988  Barr ................................. 530/350

OTHER PUBLICATIONS
Leicht et al., Nature vol. 297 pp. 655–659 Jun. 24, 1982.
Lawn et al., Cell vol. 15 pp. 1157–1174 (1978).
Maniatis et al., Cell vol. 15 pp. 687–701 Oct. 1978.
Tacon et al., Molec. Gen. Genet vol. 177, pp. 427–438 (1980).
Goeddel et al, Nature vol. 287 Oct. 2, 1980.
Bagdasarian et al., J. Clin. Invest. vol. 67, pp. 281–291 Jan. 1981.
Pannell et al., Biochemistry vol. 13 5439–5445 1974.
Kurachi et al., PNAS USA vol. 78 6826–6830 Nov. 1981.
Cannell et al., Biochem. Biophys Res. Comm. vol. 91, pp. 1032–1037 Dec. 1979.
Berman et al., Trends in Biotechnology vol. 3 No. 2 pp. 51–53 (1985).
Cabezón, et al. 1984 Proc. Natl. Acad. Sci. 81, 6594–6598.
Marglin et al. 1970, Ann. Rev. Biochem. 39, 841–866.
van der Straten et al. 1986, DNA 5, 129–136.
Bollen et al. 1983, DNA 2, 255–264.
Chandra et al. 1981, Biochem. Biophys. Res. Commun. 103, 751–758.
Owen, et al., Biochim. Biophys. Acta 453: 257–261 (1976).
Weiland, et al. Blut 44: 173–175 (1982).
Olden, et al., J. Cell, Biochem. 18: 313–335 (1982).
Bazill, et al., Biochem. J. 210: 747–759 (1983).
Dahl, et al., Science 239: 72–74 (1988).
Sairam and Bhargavi, Science 229: 65–67 (1985).
Hoffman, et al., J. Clin. Invest. 75: 1174–1182 (1985).
Sharon and Lis, Chem. Eng. News 59 (13): 21 (1981).
Karp, et al., J. Biol. Chem. 257: 7330–7335 (1982).

*Primary Examiner*—Christopher S. F. Low
*Attorney, Agent, or Firm*—Seed and Berry

[57] ABSTRACT

Promoters associated with expression of specific enzymes in the glycolytic pathway are used for expression of alien DNA, particularly yeast promoters known to provide high enzyme levels of enzymes in the glycolytic pathway are employed for expressing a mammalian protein, such as $\alpha_1$-antitrypsin. The promoters include promoters involved in expression of pyruvate kinase, triose phosphate isomerase, phosphoglucose isomerase, phosphoglycerate mutase, hexokinase 1, hexokinase 2, glucokinase, phosphofructokinase, and aldolase, as well as the glycolytic regulation gene. Particularly, the glycolytic regulation gene can be used in conjunction with promoters in the glycolytic pathway for regulated production of desired proteins.

6 Claims, 4 Drawing Sheets

```
5'G G G G G G G G G G G G G G G G A G T G A A T C G A C A

-24                      -20
       Met  Pro  Ser  Ser  Val  Ser  Trp  Gly  Ile  Leu
       A T G C C G T C T T C T G T C T C G T G G G G C A T C C T C
       +1             10                  20                  30

-10
       Leu  Leu  Ala  Gly  Leu  Cys  Cys  Leu  Val  Pro
       C T G C T G G C A G G C C T G T G C T G C C T G G T C C C T
                      40                  50                  60

-1    1
       Val  Ser  Leu  Ala  Glu  Asp  Pro  Gln  Gly  Asp
       G T C T C C C T G G C T G A G G A T C C C C A G G G A G A T
                      70                  80                  90

10
       Ala  Ala  Gln  Lys  Thr  Asp  Thr  Ser  His  His
       G C T G C C C A G A A G A C A G A T A C A T C C A C C A T
                     100                 110                 120

20
       Asp  Gln  Asp  His  Pro  Thr  Phe  Asn  Lys  Ile
       G A T C A G G A T C A C C C A A C C T T C A A C A A G A T C
                                                               150

30
       Thr  Pro  Asn  Leu  Ala  Glu  Phe  Ala  Phe  Ser
       A C C C C C A A C T T G G C T G A G T T C G C C T T C A G C
                     160                 170                 180

40
       Leu  Tyr  Arg  Gln  Leu  Ala  His  Gln  Ser  Asn
       C T A T A C C G C C A G C T G G C A C A C C A G T C C A A C
                  190                    200                 210

50
       Ser  Thr  Asn  Ile  Phe  Phe  Ser  Pro  Val  Ser
       A G C A C C A A T A T C T T C T T C T C C C C A G T G A G C
                     220                 230                 240

60
       Ile  Ala  Thr  Ala  Phe  Ala  Met  Leu  Ser  Leu
       A T C G C T A C A G C C T T T G C A A T G C T C T C C C T G
                     250                 260                 270

70
       Gly  Thr  Lys  Ala  Asp  Thr  His  Asp  Glu  Ile
       G G G A C C A A G G C T G A C A C T C A C G A T G A A A T C
                     280                 290                 300
```

FIG. 1A

```
                        80
     Leu   Glu   Gly   Leu   Asn   Phe   Asn   Leu   Thr   Glu
     C T G G A G G G C C T G A A T T T C A A C C T C A C G G A G
              310               320               330

90
     Ile   Pro   Glu   Ala   Gln   Ile   His   Glu   Gly   Phe
     A T T C C G G A G G C T C A G A T C C A T G A A G G C T T C
              340               350               360

100
     Gln   Glu   Leu   Leu   Arg   Thr   Leu   Asn   Gln   Pro
     C A G G A A C T C C T C C G T A C C C T C A A C C A G C C A
              370               380               390

110
     Asp   Ser   Gln   Leu   Gln   Leu   Thr   Thr   Gly   Asn
     G A C A G C C A G C T C C A G C T G A C C A C C G G C A A T
              400               410               420

120
     Gly   Leu   Phe   Leu   Ser   Glu   Gly   Leu   Lys   Leu
     G G C C T G T T C C T C A G C G A G G G C C T G A A G C T A
              430               440               450

130
     Val   Asp   Lys   Phe   Leu   Glu   Asp   Val   Lys   Lys
     G T G G A T A A G T T T T T G G A G G A T G T T A A A A A G
              460               470               480

140
     Leu   Tyr   His   Ser   Glu   Ala   Phe   Thr   Val   Asn
     T T G T A C C A C T C A G A A G C C T T C A C T G T C A A C
              490               500               510

150
     Phe   Gly   Asp   Thr   Glu   Glu   Ala   Lys   Lys   Gln
     T T C G G G G A C A C C G A A G A G G C C A A G A A A C A G
              520               530               540

160
     Ile   Asn   Asp   Tyr   Val   Glu   Lys   Gly   Thr   Gln
     A T C A A C G A T T A C G T G G A G A A G G G T A C T C A A
              550               560               570

170
     Gly   Lys   Ile   Val   Asp   Leu   Val   Lys   Glu   Leu
     G G G A A A A T T G T G G A T T T G G T C A A G G A G C T T
              580               590               600

180
     Asp   Arg   Asp   Thr   Val   Phe   Ala   Leu   Val   Asn
     G A C A G A G A C A C A G T T T T T G C T C T G G T G A A T
              610               620               630
```

FIG. 1B

```
              190
Tyr  Ile  Phe  Phe  Lys  Gly  Lys  Trp  Glu  Arg
T A C A T C T T C T T T A A A G G C A A A T G G G A G A G A
          640            650              660

200
Pro  Phe  Glu  Val  Lys  Asp  Thr  Glu  Glu  Glu
C C C T T T G A A G T C A A G G A C A C C G A G G A A G A G
          670            680              690

210
Asp  Phe  His  Val  Asp  Gln  Val  Thr  Thr  Val
G A C T T C C A C G T G G A C C A G G T G A C C A C C G T G
          700            710              720

220
Lys  Val  Pro  Met  Met  Lys  Arg  Leu  Gly  Met
A A G G T G C C T A T G A T G A A G C G T T T A G G C A T G
          730            740              750

230
Phe  Asn  Ile  Gln  His  Cys  Lys  Lys  Leu  Ser
T T T A A C A T C C A G C A T T G T A A G A A G C T G T C C
          760            770              780

240
Ser  Trp  Val  Leu  Leu  Met  Lys  Tyr  Leu  Gly
A G C T G G G T G C T G C T G A T G A A A T A C C T G G G C
          790            800              810

250
Asn  Ala  Thr  Ala  Ile  Phe  Phe  Leu  Pro  Asp
A A T G C C A C C G C C A T C T T C T T C C T G C C T G A T
          820            830              840

260
Glu  Gly  Lys  Leu  Gln  His  Leu  Glu  Asn  Glu
G A G G G A A A A C T A C A G C A C C T G G A A A A T G A A
          850            860              870

270
Leu  Thr  His  Asp  Ile  Ile  Thr  Lys  Phe  Leu
C T C A C C C A C G A T A T C A T C A C C A A G T T C C T G
          880            890              900

280
Glu  Asn  Glu  Asp  Arg  Arg  Ser  Ala  Ser  Leu
G A A A A T G A A G A C A G A A G G T C T G C C A G C T T A
          910            920              930

290
His  Leu  Pro  Lys  Leu  Ser  Ile  Thr  Gly  Thr
C A T T T A C C C A A A C T G T C C A T T A C T G G A A C C
          940            950              960
```

FIG. 1C

```
                        300
  Tyr  Asp  Leu  Lys  Ser  Val  Leu  Gly  Gln  Leu
  T A T G A T C T G A A G A G C G T C C T A G G T C A A C T G
            970              980              990

310
  Gly  Ile  Thr  Lys  Val  Phe  Ser  Asn  Gly  Ala
  G G C A T C A C T A A G G T C T T C A G C A A T G G G C T
            1000             1010             1020

320
  Asp  Leu  Ser  Gly  Val  Thr  Glu  Glu  Ala  Pro
  G A C C T C T C C G G G G T C A C A G A G G A G G C A C C C
            1030             1040             1050

330
  Leu  Lys  Leu  Ser  Lys  Ala  Val  His  Lys  Ala
  C T G A A G C T C T C C A A G G C C G T G C A T A A G G C T
            1060             1070             1080

340
  Val  Leu  Thr  Ile  Asp  Glu  Lys  Gly  Thr  Glu
  G T G C T G A C C A T C G A C G A G A A A G G G A C T G A A
            1090             1100             1110

350
  Ala  Ala  Gly  Ala  Met  Phe  Leu  Glu  Ala  Ile
  G C T G C T G G G G C C A T G T T T T T A G A G G C C A T A
            1120             1130             1140

360
  Pro  Met  Ser  Ile  Arg  Pro  Glu  Val  Lys  Phe
  C C C A T G T C T A T C C G C C C C G A G G T C A A G T T C
            1150             1160             1170

370
  Asn  Lys  Pro  Phe  Val  Phe  Leu  Met  Ile  Glu
  A A C A A A C C C T T T G T C T T C T T A A T G A T T G A A
            1180             1190             1200

380
  Gln  Asn  Thr  Lys  Ser  Pro  Leu  Phe  Met  Gly
  C A A A A T A C C A A G T C T C C C C T C T T C A T G G G A
            1210             1220             1230

390                394
  Lys  Val  Val  Asn  Pro  Thr  Gln  Lys  STOP
  A A A G T G G T G A A T C C C A C C C A A A A A T A A C T G
            1240             1250

GLYCOLYTIC PROMOTERS FOR REGULATED PROTEIN EXPRESSION: PROTEASE INHIBITOR

CROSS-REFERENCE TO RELATED APPLICATION

This application is a continuation of U.S. application Ser. No. 07/387,366, filed Jul. 26, 1989, now abandoned, which is a continuation of U.S. application Ser. No. 06/868,423 filed May 29, 1986, now abandoned, which is a division of application Ser. No. 408,099 filed Aug. 13, 1982, now U.S. Pat. No. 4,599,311.

BACKGROUND OF THE INVENTION

1. Field of the Invention

The ability to obtain expression of foreign, i.e., exogenous, DNA in unicellular microorganisms provided the opportunity to conveniently prepare long polypeptide chains of interest. Almost immediately, varied polypeptides, such as the small hormone somatostatin and more sophisticated polypeptides, such as insulin, interferons, thymosin and a variety of vaccines having capsid proteins, were prepared and reported in the literature. For the most part, the initial work was performed in the bacterium E. coli which had been the subject of intensive study because scientists were familiar with many aspects of its genetic structure and properties. Initial attention was therefore directed to producing foreign proteins in E. coli. Once the ability to employ E. coli as a host was established, the limitations and disadvantages of employing E. coli encouraged the use of other hosts.

One host which appeared to be particularly attractive because it lacked many of the shortcomings of E. coli was yeast. However, yeast is a eukaryote and, therefore, has a more sophisticated genetic system. Furthermore, less is known about the yeast genome than is known about E. coli. In order to use yeast as a host for the production of proteins foreign to yeast, a number of discoveries are required, and new materials must be made available.

Initially, a replication system was required which provided stability in yeast, either as an extrachromosomal element or by integration into the yeast chromosome. In addition, the regulatory functions concerned with transcription and expression had to be developed in order to allow for expression of the desired protein. There was also the uncertainty whether foreign DNA sequences would be transcribed and translated and, if expressed, whether the resulting polypeptides would survive in the yeast cell. Also remaining to be determined was the effect of the foreign proteins on the viability of the yeast cell, such as the effect of recombinant DNA (RDNA) on mitosis, sporulation and vegetative growth.

There have, therefore, been substantial efforts to develop novel RDNA systems in yeast, which will allow for regulated expression of a protein of interest, as well as highly efficient production of such proteins.

2. Description of the Prior Art

Hitzeman et al., J. Biol. Chem. (1980) 255:12073–12080 describe a plasmid having a yeast 3-phosphoglycerate kinase (PGK) gene and accompanying regulatory signals capable of expression in yeast. Other references of interest include Clifton, et al., Genetics (1978) 88:1–11; Clark and Carbon, Cell (1976) 9:91–99; Thomson, Gene (1977) 1:347–356; Holland and Holland, J. Biol. Chem. (1979) 254:5466–5474; Holland and Holland, ibid. (1979) 254:9830–9845; Nasmyth and Reed, Proc. Nat. Acad. Sci. (1980) 77:2119–2123; Broach, et al., Gene (1979) 8:121–133; and Williamson, et al., Nature (1980) 283:214–216.

BRIEF DESCRIPTION OF THE DRAWING

FIGS. 1A through 1D illustrates the cDNA sequence and derived amino acid sequence for one form of human alpha-1-antitrypsin.

SUMMARY OF THE INVENTION

Novel yeast promoters are provided which control the transcription of genes in the glycolytic pathway and which find use in the regulated production of proteins foreign to the yeast. Promoters of particular interest include the promoters for triose phosphate isomerase, pyruvate kinase, phosphoglucose isomerase, phosphoglycerate mutase, hexokinase 1, hexokinase 2, glucokinase, phosphofructokinase, and aldolase, as well as the glycolytic regulatory gene. The protease inhibitor, mammalian $\alpha_1$-antitrypsin, is expressed using the promoter for triose phosphate isomerase.

DESCRIPTION OF THE SPECIFIC EMBODIMENTS

Methods and compositions are provided for regulated efficient expression of alien or foreign DNA in a yeast host. (Alien or foreign DNA is DNA not naturally occurring in the wild type particularly from a different species and which does not normally exchange genetic information with the host.) Novel promoters are employed which are involved in the glycolytic pathway and provide for high levels of protein production, so that a substantial proportion of the total protein produced by the yeast cells can be dedicated to the protein of interest. In addition, regulatory mechanisms associated with regulation of production of the glycolytic enzymes are achieved, so that production of the desired products may be modulated. Furthermore, viable cells can be maintained to enhance the efficiency and amount of expression.

The promoters of interest are particularly those promoters involved with expression of triose phosphate isomerase, pyruvate kinase, phosphoglucose isomerase, phosphoglycerate mutase, hexokinase 1, hexokinase 2, glucokinase, phosphofructokinase, and aldolase, which are controlled by the glycolytic regulation gene GCR1. The genes of the glycolytic pathway include hexokinase 1 and 2 (HXK1,2); phosphoglucose isomerase (PGI, triose phosphate isomerase (TPI): phosphoglycerate kinase (PGK), phosphoglycerate mutase (GPM), pyruvate kinase (PYK); phosphofructokinase (PFK), enolase (ENO); fructose 1,6-diphosphate aldolase (FDA); glyceraldehyde 3-phosphate dehydrogenase (PGK); and glycolysis regulation protein (GCR).

The promoters may be obtained by employing a gene bank having large fragments of yeast DNA. By introducing the fragments into appropriate vectors, particularly shuttle vectors having replicons for prokaryotes and yeast, one can readily amplify and clone the yeast DNA in a bacterium and then introduce the yeast DNA into mutant yeast cells for complementation. In this manner, yeast fragments can be identified which complement auxotrophic lesions or mutations in a yeast host.

Of particular interest, is where the host is auxotrophic in both the glycolytic pathway step of interest and a separate biochemical pathway, which is complemented by a marker in the vector. Once having established a DNA segment having the desired gene, one may reclone by various techniques to shorten the DNA segment and provide for a segment which is primarily the gene of interest in conjunction with its regulatory signals for transcription and expression.

In order to retain the promoter, it is essential that the initiator methionine be determined and this codon be used for developing the strategy for introducing the alien DNA downstream from the promoter. Various techniques can be employed for providing a site for introduction of the alien DNA so as to be under the regulatory control of the promoter in the glycolytic pathway.

Where a restriction site is conveniently adjacent to the initiator methionine codon, the glycolytic gene may be cleaved at that site and the DNA chewed back with Bal31 for varying periods of time, so as to chew into or past the initiator methionine codon or retain the initiator methionine codon.

Where there is no convenient restriction site, other splicing techniques such as primer repair may be employed. Also, by employing in vitro mutagenesis, one can introduce a restriction site adjacent the initiator methionine, which encodes for the initial amino acids of the desired protein. In each instance, a linearized DNA segment is obtained having the intact promoter for the glycolytic product and normally includes other DNA sequences, such as an intact replicon, one or more markers, and the like.

Exemplary of the above procedure is the development of a vector having the promoter for the TPI1 gene. An exemplary vector CV13 having the replicons or replication systems from pBR322 and 2μ-plasmid of yeast, as well as the LEU2 gene was employed for insertion of a yeast fragment which was shown to have the TPI1 gene. This was achieved by employing double selection with a mutant yeast which was leu⁻, tpi⁻ The TPI1 gene was found to have a unique KpnI site. The vector was cleaved at the KpnI site and then treated with the double stranded exonuclease Bal31 for varying times to chew back the DNA to about the f-met codon. Linkers were then inserted providing desired restriction sites. Alien DNA could then be inserted providing a sequence having a f-met codon in the appropriate position for initiation. Alternatively, the foreign DNA can be expressed using the f-met codon of the TPI1 gene.

Similar procedures can be performed with the other subject glycolytic genes in order to provide the promoters associated with those genes. The PYK sequence has a convenient XbaI site for restriction, where the few additional bases may be removed, if required, using Bal31 for a short period of time to chew to or through the methionine codon. Of particular interest is the use of the GCR promoter to control the expression of the other genes involved in the glycolytic pathway. By employing the GCR gene, in conjunction with other glycolytic promoters regulating expression of alien DNA, one can turn on and off the other promoters, so as to regulate the expression of the alien DNA. Thus, one can allow vegetative growth to proceed until a desired cell density is achieved, before permitting production of the desired polypeptide.

By employing appropriate auxotrophs, one can further regulate the expression of the polypeptides of interest in choosing the appropriate nutrient medium. Where the chosen promoter is repressed by the particular nutrient because of a metabolic block, a change in the nature of the nutrient can induce expression. Furthermore, the activity of a number of promoters in the glycolytic pathway can be affected by the repression or activation of expression by the GCR gene or other regulatory controls. Also, the GCR regulatory signals can be used to titrate the polypeptide functioning as the regulator for expression of GCR. By having vectors whose copy number can be controlled, one can vary the activity of the wild type GCR gene.

In order to obtain expression, an extrachromosomal element construct will be prepared having a number of sequences defining different functions. One function is the replication system, which forms part of a vector. Another function is a promoter by itself or in conjunction with the alien DNA. Other functions include initiators and terminators of expression. Also, there will be selectable markers.

In developing an appropriate vector, while not necessary, it will be common to have both a replication system for yeast and a replication system for a prokaryote (a shuttle vector). The replication system for yeast may be one which provides for stable maintenance of an extrachromosomal element or one which provides a sufficient lifetime for the DNA in the host, that there is an acceptable probability of integration of the DNA into the host. Integration can be greatly aided by providing for a sequence homologous to the host DNA, so as to provide for recombination. Generally, the homologous sequence will be at least about 800 bp usually not more than about 2000 bp. Therefore, either integration or an autonomous replication system, such as the use of the ARS1 gene, may be employed to provide for the maintenance of the alien DNA in the yeast host. The replication system which is chosen should provide for a reasonable copy number usually greater than 1, preferably greater than 5. A wide variety of replication systems are available on a wide variety of prokaryotic vectors, such as pBR322, pACYC184, pSC101, pMB9, etc. Alternatively, one or more copies of the DNA construct can be integrated into the host chromosome. The replication systems may also be conditionally regulated, usually being temperature sensitive so that replication can be turned on and off by varying the temperature.

In addition to the replication system, there will also be one or more selectable markers, there usually being at least one marker in addition to the alien DNA, which may serve as a marker. Conventional markers include biocidal markers providing antibiotic resistance and those providing resistance to toxins and heavy metals. Also useful is employing an auxotrophic host and providing prototrophy by complementation. In addition to the conventional selection systems just described, the glycolytic genes of the present invention are particularly desirable markers since they can provide for selection, using sugars as selective substrates, in appropriate mutant host strains.

Other genes may also be inserted into the extrachromosomal element for a variety of purposes. Where integration is desirable in the genome of the host, a homologous sequence for a particular region of the host genome may be included in the extrachromosomal element. Where amplification of one or more sequences is desired, genes known to provide such amplification, such as dihydrofolate reductase genes, which respond to methotrexate stress or metallothionein genes, which respond to heavy metal stress, may be included in the extrachromosomal element, flanked by the DNA regions to be reiterated. Other regulatory signals may also be included, such as centromeres, autonomously replicating segments, etc.

In order to isolate the promoters of interest, clones can be made of yeast chromosomal DNA by random digestion or mechanical shearing of the yeast genome. The presence of the desired gene is then determined by introducing a homogeneous clone of a yeast fragment into an auxotrophic host for complementation. Desirably, the cloning vehicle may have another gene which allows for an additional basis for selection, so that double selection techniques can be used. The mutants are substantially incapable of growing on limited nutrient medium, so that one can select for the presence of the desired glycolytic gene by the choice of medium. After isolating the yeast fragment having the desired gene, the fragment may be subcloned so as to remove superfluous DNA flanking regions and provide for a fragment which is more easily manipulated. The smaller fragment containing the desired gene, of a size less than about 500 base pairs may then be further cloned, restriction mapped and sequenced, so as to provide a useful source for the desired promoters and insertion of the alien DNA. Also, as indicated, the promoters in themselves may be useful, in acting as a titrater for repressor or activator, where it is desirable to modulate the production of a particular enzyme in the yeast host.

The alien DNA may be from any source, either naturally occurring or synthetic, either prokaryotic or eukaryotic. Of particular interest are mammalian genes which express a poly(amino acid), that is, polypeptide or protein which has physiological activity. To varying degrees, poly(amino acids) prepared in yeast may be modified by glycosylation, where the glycosylation may not occur or may occur at different sites from the naturally occurring mammalian polypeptide and/or in different degrees with different saccharides. It is therefore of great interest to be able to prepare polypeptides which are different from the naturally occurring polypeptide by the degree and manner of glycosylation and in many instances may differ in one or more ways as to the amino acid sequences, where there may be deletions of one or more amino acids or substitutions of one or more amino acids. Mammalian genes may come from a wide variety of mammalian sources, such as domestic animals (e.g. bovine, porcine, ovine and equine) and primates e.g. humans and monkeys.

As exemplary of the use of the subject promoters in preparing an active polypeptide composition, as well as being of particular interest for a variety of, purposes, a protease inhibitor is described and made. The protease inhibitor has the same or substantially the same amino acid sequence of human $\alpha_1$-antitrypsin and is capable of inhibiting a number of proteolytic enzymes. The human $\alpha_1$-antitrypsin gene appears to reside within a 9.6 kb EcoRI DNA fragment in the human genome. The mature mRNA appears to have about 1400 nucleotides. One human $\alpha_1$-antitrypsin cDNA has the following sequence, although other naturally-occurring forms (polymorphisms) are known.

The human $\alpha_1$-AT has a BamHI restriction site which allows the cutting of the gene with the removal of information for a single glutamic acid from the mature protein. Various schemes can be employed for introducing the human $\alpha_1$-AT gene adjacent the glycolytic promoter to be under the regulation of the promoter. Where the promoter does not have a convenient restriction site near the f-met codon, the glycolytic gene may be cleaved and chewed back to the promoter with Bal31. A linker may then be introduced downstream from the promoter to provide a convenient cohesive end or flush end for joining to the human $\alpha_1$-AT gene. The linker can also provide one or more codons for amino acids at the N-terminus of the $\alpha_1$-AT gene, which may be the same or different from the naturally occurring amino acids.

The gene for human $\alpha_1$-AT may then be inserted into the extrachromosomal element downstream from the glycolytic promoter, where an f-met codon is provided for initiation of expression of the human $\alpha_1$-AT.

The resulting extrachromosomal element containing the human $\alpha_1$-AT gene may then be introduced into a yeast host, particularly an auxotrophic host and the yeast host grown for expression of a polypeptide having $\alpha_1$-antitrypsin activity. The resulting polypeptide differs from the naturally occurring human $\alpha_1$-AT in its degree of glycosylation.

The $\alpha_1$-antitrypsin can be used as an antigen for production of polyclonal and monoclonal antibodies to human $\alpha_1$-AT, for introduction into a host having a deficiency of $\alpha_1$-AT, or for modulating proteolytic activity in a mammalian host. In particular, the $\alpha_1$-antitrypsin can be administered to humans to replace $\alpha_1$-antitrypsin which has been inactivated (oxydized) by tobacco and other smoke.

The following examples are offered by way of illustration and not by way of limitation.

EXPERIMENTAL

Materials and Methods

Strains. Isogenic strains carrying mutations in PGI1, PGK1, GPM1, PYK1, and GCR1 where obtained by ethyl methane sulfonate (EMS) mutagenesis of S. cerevisiae (S. c.) X2180-1A (MATa SUC2 CUP1 gal2, from the Berkeley Yeast Stock Center). 35,000 independent colonies were grown on YEP-3% glycerol-2% ethanol and were screened by replica plating for the inability to grow on YEP-4% dextrose (Table 1).

Identification of specific lesions was made by complementation tests with known glycolysis mutants (Ciriacy and Breitenbach (1979) J.Bacteriol. 139:152-60), while at least 15 additional complementation groups were found by intercrossing mutant strains. Enzyme assays (Clifton et al. (1980) Genetics 88:1-11) confirmed the glycolytic defects in pgi1, pgk1, gpm1, pyk1, and gcr1 mutants.

A leu2 mutant was also derived from S. cerevisiae X2180-1A by EMS treatment and was crossed to X2180-1B (an isogenic MATα strain) to produce N501-1B MATα leu2 SUC2 CUP1 gal2). Cycloheximide (cyh2) and canavanine (can1) resistances were then selected as spontaneous mutations in N501-1B. The glycolysis mutants were crossed to N501-1B to produce a series of isogenic leu2 strains each defective in a single glycolytic function or in GCR1.

A tpi1 mutant, S. cerevisiae GLU77 was crossed to N551-1A (MATa leu2 SUC2 CUP1 gal2); strains derived from this mating were crossed twice to N501-1B to produce a tpi1 leu2 strain, N587-2D, which was similar in genetic background to the other glycolysis mutants.

Mutations in three glucose phosphorylating enzymes produce a strain which is unable to grow on dextrose as the sole carbon source and which is resistant to catabolite repression by 2-deoxyglucose and glucosamine.

N517-6C (hxk1 hxk2 glk1 leu2 can1-100 cyh2 ade2-1) was derived from a hxk1 hxk2 glk1 strain, D308.3, by screening for glucosamine-resistant spore colonies. Defects in glucose kinasing activities were confirmed by assay.

TABLE 1

Complementation Groups of glu⁻ Derivatives of X2180-1A

| Gene | No. of Mutants |
|---|---|
| PYK1 | 14 |
| PDC1 | 9 |
| GCR1 | 4 |
| PGI1 | 3 |
| GPM1 | 3 |
| PGK1 | 1 |
| TPI1 | 0 |
| FDP | 0 |
| (LEU2) | (1) |
| I | 11 |
| II | 10 |
| III | 3 |
| IV | 5 |
| V | 1 |
| VI | 1 |

TABLE 1-continued

Complementation Groups of glu⁻ Derivatives of X2180-1A

| Gene | No. of Mutants | |
|---|---|---|
| VII | 2 | |
| VIII | 3 | 60 other mutations not in |
| IX | 2 | the complementation groups |
| X | 3 | |
| XI | 2 | |
| XII | 1 | |
| XIII | 1 | |
| XIV | 5 | |
| XV | 1 | |

27 sterile glu⁻ strains
35,000 colonies screened (EMS mutagenized for 50% kill)

The homothallic diploid strain, *S. c.* AB320 was the source of the yeast DNA pool (Nasmyth and Reed, Proc. Nat. Acad. Sci. (1980) 77:2119-2123) and was used as a control in some experiments.

The triose phosphate isomerase gene (including the upstream sequence having the regulator signals) is as follows:

```
         G A A T C C A T C A A T A G A T A C G T C C T G A G G A C C G T G C T A C C C A A A T G G A C T G A T T G T G A G G G A
       -658       -650       -640       -630       -620       -610       -600

G A C C T A A C T A C A T A G T G T T T A A G A T T A C G G A T A T T T A C T T A C T T A G A A T A A T G C C A T T T
       -590       -580       -570       -560       -550       -540

T T T T G A G T T A T A A T A A T C C T A C G T T A G T G T G A G C G G G A T T T A A A C T G T G A G G A C C T T A A T
       -530       -520       -510       -500       -490       -480

A C A T T C A G A C A C T T C T G A C G G T A T C A C C C T A C T T A T T C C C T T C G A G A T T A T A T C T A G G A A
       -470       -460       -450       -440       -430       -420

C C C A T C A G G T T G G T G G A A G A T T A C C C G T T C T A A G A C T T T T C A G C T T C C T C T A T T G A T G T T
       -410       -400       390       -380       -370       -360

A C A C T T G G A C A C C C C T T T T C T G G C A T C C A G T T T T T A A T C T T C A G T G G C A T G T G A G A T T C T
       -350       -340       -330       -320       -310       -300

C C G A A A T T A A T T A A A G C A A T C A C A C A A T T C T C T C G G A T A C C A C C T C G G T T G A A A C T G A C A
       -290       -280       -270       -260       -250       -240

G G T G G T T T G T T A C G C A T G C T A A T G C A A A G G A G C C T A T A T A C C T T T G G C T C G G C T G C T G T A
       -230       -220       -210       -200       -190       -180

A C A G G G A A T A T A A A G G G C A G C A T A A T T T A G G A G T T T A G T G A A C T T G C A A C A T T T A C T A T T
       -170       -160       -150       -140       -130       -120

T T C C C T T C T T A C G T A A A T A T T T T T C T T T T T A A T T C T A A A T C A A T C T T T T T C A A T T T T T T G
       -110       -100        -90        -80        -70        -60

MET
         T T T G T A T T C T T T T C T T G C T T A A A T C T A T A A C T A C A A A A A A C A C A T A C A T A A A C T A A A A A T
        -50        -40        -30        -20        -10        -11

ALA ARG THR PHE PHE VAL GLY GLY ASN PHE LYS LEU ASN GLY SER  LYS GLN SER ILE  LYS
    G G C T A G A A C T T T C T T T G T C G G T G G T A A C T T T A A A T T A A A C G G T T C C A A A C A A T C C A T T A A
           10          20          30          40          50          60

GLU  ILE VAL GLU ARG LEU ASN THR ALA SER  ILE PRO GLU ASN VAL GLU VAL VAL ILE CYS
    G G A A A T T G T T G A A A G A T T G A A C A C T G C T T C T A T C C C A G A A A A T G T C G A A G T T G T T A T C T G
           70          80          90         100         110         120

PRO PRO ALA THR TYR LEU ASP TYR SER VAL SER LEU VAL LYS LYS  PRO GLN VAL THR VAL
    T C C T C C A G C T A C C T A C T T A G A C T A C T C T G T C T C T T T G G T T A A G A A G C C A C A A G T C A C T G T
          130         140         150         160         170         180

GLY ALA GLN ASN ALA TYR LEU LYS ALA SER GLY ALA  PHE THR GLY GLU ASN SER  VAL ASP
    C G G T G C T C A A A A C G C C T A C T T G A A G G C T T C T G G T G C T T T C A C C G G T G A A A A C T C C G T T G A
          190         200         210         220         230         240

GLN ILE LYS ASP  VAL GLY ALA LYS TRP VAL ILE LEU GLY HIS SER GLU ARG ARG SER TYR
    C C A A A T C A A G G A T G T T G G T G C T A A G T G G G T T A T T T T G G G T C A C T C C G A A A G A A G A T C T T A
          250         260         270         280         290         300
```

-continued

```
  PHE HIS  GLU ASP ASP LYS PHE ILE ALA ASP LYS THR LYS PHE ALA LEU GLY GLN GLY VAL
  CTTCCACGAAGATGACAAGTTCATTGCTGACAAGACCAAGTTCGCTTTAGGTCAAGGTGT
     310       320       330       340       350       360

GLY VAL ILE LEU CYS  ILE GLY GLU THR LEU GLU GLU LYS LYS ALA GLY LYS THR LEU ASP
  CGGTGTCATCTTGTGTATCGGTGAAACTTTGGAAGAAAAGAAGGCCGGTAAGACTTTGGA
     370       380       390       400       410       420

VAL VAL GLU ARG GLN LEU ASN ALA VAL LEU GLU GLU VAL LYS ASP TRP THR ASN VAL VAL
  TGTTGTTGAAAGACAATTGAACGCTGTCTTGGAAGAAGTTAAGGACTGGACTAACGTCGT
     430       440       450       460       470       480

VAL ALA TYR GLU PRO VAL TRP ALA  ILE GLY THR GLY LEU ALA ALA THR PRO GLU ASP ALA
  TGTCGCTTACGAACCAGTCTGGGCCATTGGTACCGGTTTGGCTGCTACTCCAGAAGATGC
     490       500       510       520       530       540

GLN ASP  ILE HIS  ALA SER ILE ARG LYS PHE LEU ALA SER LYS LEU GLY ASP LYS ALA ALA
  TCAAGATATTCACGCTTCCATCAGAAAGTTCTTGGCTTCCAAGTTGGGTGACAAGGCTGC
     550       560       570       580       590       600

SER GLU LEU ARG  ILE LEU TYR GLY GLY SER ALA ASN GLY SER ASN ALA VAL THR PHE LYS
  CAGCGAATTGAGAATCTTATACGGTGGTTCCGCTAACGGTAGCAACGCCGTTACCTTCAA
     610       620       630       640       650       660

ASP LYS ALA ASP VAL ASP GLY PHE LEU VAL GLY GLY ALA SER LEU LYS PRO GLU PHE  VAL
  GGACAAGGCTGATGTCGATGGTTTCTTGGTCGGTGGTGCTTCTTTGAAGCCAGAATTTGT
     670       680       690       700       710       720

ASP  ILE ILE ASN SER ARG ASN ***
  TGATATCATCAACTCTAGAAACTAAGATTAATATAATTATATAAAAATATTATCTTCTTT
     730       740      747 +1       +10        +20       +30

TCTTTATATCTAGTGTTATGTAAAATAAATTGATGACTACGGAAAGCTTTTTTATATTGT
     +40       +50       +60       +70       +80       +90

TTCTTTTTCATTCTGAGCCACTTAAATTTCGTGAATGTTCTTGTAAGGGAGCGTAGATTT
     +100      +110      +120      +130      +140      +150

ACAAGTGATACAACAAAAAGCAAGGCGCTTTTTCTAATAAAAGAAGAAAAGCATTTAAC
     +160      +170      +180      +190      +200      +210

AATTGAACACCTCTATATCAACAGAAGA
     +220      +230      +240
```

The pyruvate kinase gene upstream sequence having the regulatory signals is as follows:

```
         10         20         30         40         50         60
GAATTCAGCA TGATAGCTAC GTAAATGTGT TCCGCACCGT CACAAAGTGT TTTCTACTGT
CTTAAGTCGT ACTATCGATG CATTTACACA AGGCGTGGCA GTGTTTCACA AAAGATGACA 70         80         90        100        110        120
TCTTTCTTCT TTCGTTCATT CAGTTGAGTT GAGTGAGTGC TTTGTTCAAT GGATCTTAGC
AGAAAGAAGA AAGCAAGTAA GTCAACTCAA CTCACTCACG AAACAAGTTA CCTAGAATCG 130        140        150        160        170        180
TAAAATGCAT ATTTTTTCTC TTGGTAAATG AATGCTTGTG ATGTCTTCCA AGTGATTTCC
ATTTTACGTA TAAAAAAGAG AACCATTTAC TTACGAACAC TACAGAAGGT TCACTAAAGG 190        200        210        220        230        240
TTTCCTTCCC ATATGATGCT AGGTACCTTT AGTGTCTTCC TAAAAAAAAA AAAAGGCTCG
AAAGGAAGGG TATACTACGA TCCATGGAAA TCACAGAAGG ATTTTTTTTT TTTTCCGAGC 250        260        270        280        290        300
CCATCAAAAC GATATTCGTT GGCTTTTTTT TCTGAATTAT AAATACTCTT TGGTAACTTT
GGTAGTTTTG CTATAAGCAA CCGAAAAAAA AGACTTAATA TTTATGAGAA ACCATTGAAA 310        320        330        340        350        360
TCATTTCCAA GAACCTCTTT TTTCCAGTTA TATCATGGTC CCCTTTCAAA GTTATTCTCT
AGTAAAGGTT CTTGGAGAAA AAAGGTCAAT ATAGTACCAG GGGAAAGTTT CAATAAGAGA 370        380        390        400        410        420
ACTCTTTTTC ATATTCATTC TTTTTCATCC TTTGGTTTTT TATTCTTAAC TTGTTTATTA
TGAGAAAAAG TATAAGTAAG AAAAAGTAGG AAACCAAAAA ATAAGAATTG AACAAATAAT 430        440        450        460        470        480
TTCTCTCTTG TTTCTATTTA CAAGACACCA ATCAAAACAA ATAAAACATC ATCACAATGT
AAGAGAGAAC AAAGATAAAT GTTCTGTGGT TAGTTTTGTT TATTTTGTAG TAGTGTTACA
```

-continued

```
        490         500         510         520         530         540
CTAGATTAGA AAGATTGACC TCATTAAACG TTGTTGCTGG TTCTGACTTG AGAAGAACCT
GATCTAATCT TTCTAACTGG AGTAATTTGC AACAACGACC AAGACTGAAC TCTTCTTGGA 550         560         570         580         590         600
CCATCATTGG TACCATCGGT TCAAAGACCA ACAACCCAGA AACCTTGGTT GCTTTGAGAA
GGTAGTAACC ATGGTAGCCA AGTTTCTGGT TGTTGGGTCT TTGGAACCAA CGAAACTCTT 610         620         630         640         650         660
AGGCTGGTTT GAACATTGTT CGTATGAACT TCTCTCACGG TTCTTACGAA TACCACAAGT
TCCGACCAAA CTTGTAACAA GCATACTTGA AGAGAGTGCC AAGAATGCTT ATGGTGTTCA 670         680         690         700
CTGTCGTTGA CAACGCCAGA AAGTCCGAAG AATTGTACCC
GACAGCAACT GTTGCGGTCT TCAGGCTTC TTAACATGGG
```

Screening of clone bank. The leu2 glycolysis mutants were transformed with a yeast DNA pool inserted into pYE13, a high copy plasmid carrying a selectable LEU2 wild-type gene (Broach et al., Gene (1979) 8:121-133). The glycolytic genes were obtained by complementation, involving the simultaneous selection for growth on glucose and leucine prototrophy. A synthetic medium containing yeast nitrogen base, 4% glucose, and the following supplements was used: per liter, 40 mg adenine, 20 mg arginine, 50 mg aspartate, 10 mg histidine, 60 mg isoleucine, 40 mg lysine, 10 mg methionine, 60 mg phenylalanine, 50 mg threonine, 40 mg tryptophan, 50 mg tyrosine, 20 mg uracil, and 60 mg valine.

The transformants were purified on leucineless media and were then grown on a non-selective medium (YEPGE) to allow mitotic segregation of the plasmids. Strains which cosegregated the leu2 and glycolysis mutant phenotypes, as determined by replica plating on selective media, were assayed for glycolytic enzyme activities. Yeast DNA preps were made, and the E. coli strain, RR1, was transformed, selecting for ampicillin resistance, to verify the presence of plasmid DNAs in these yeast glycolytic transformants.

Enzyme Assays. The transformed yeast strains were selectively grown on minimal medium with 8% glucose (adenine was added to a final concentration of 50 mg/l). The wild-type control, N501-1B, was grown on the same medium plus leucine (100 mg/l). The glycolysis mutant strains were grown on YEP-5% glycerol-1% lactate. Overnight cultures were fed fresh media and were aerobically grown at 30° for four hours before harvesting. The cells were washed two times with water and resuspended in 50 mM $K_2$mM EDTA 3 mM 2-mercaptoethanol (adjusted to pH7.4 with HCl). Extracts were obtained by vortexing the cells with an equal volume of glass beads (0.45 mm diam.) at high speed for two minutes. The cell debris was removed by centrifugation in a microfuge for 15 min. at 4°. Enzymes were assayed as described by Clifton and Breitenbach, supra. Protein concentrations were determined by the Biuret-TCA method.

In order to determine the activity of the various glycolytic genes in the transformants, the various enzymes were assayed and the results for the transformants were compared to mutant and wild-type strains. The gcr1 mutant had 5-10% of the wild-type levels of most glycolytic activities (exemplified by PGI, aldolase and enolase) and grows very poorly on glucose media. In contrast, the GCR1 transformants had nearly wild-type levels of enzymes and were virtually identical to wild-type for growth on glucose media. The other glycolysis mutants had less than 5% of the normal levels of their respective enzyme activities. However, when transformed with a complementing high copy plasmid, the specific enzyme activities were substantially elevated above wild-type levels (typically 5-10 fold higher). The following Table 2 indicates the results.

TABLE 2

Comparison of Glycolytic Activities in Wild-type, Mutant, and Transformed Strains

| Enzyme | Activities | | | Ratio: |
| --- | --- | --- | --- | --- |
| | Wild-type[a] | Mutant[b] | Transformant[c] | Transf/Wt |
| PGI | 2.85 | .0065 | 31.49 (10) | 11.1 |
| TPI | 18.3 | .0000 | 167.8 (10) | 9.2 |
| PGK | 1.99 | .0046 | 17.67 (3) | 8.9 |
| GPM | 0.74 | .0000 | 4.80 (10) | 6.5 |
| PYK | 4.02 | .0057 | 14.77 (10) | 3.7 |

| | Wild-type[a] | gcr1 Mutant[d] | GCR1 Transf[c] | |
| --- | --- | --- | --- | --- |
| PGI | 2.85 | .2436 | 2.42 (10) | .85 |
| Aldolase | 4.33 | .4415 | 2.96 (10) | .68 |
| Enolase | 0.43 | .0274 | .316 (10) | .74 |

[a]Wild-type is N501-1B.
[b]The respective mutant strains are N543-9D (pgi1 leu2), N587-2D (tpi1 leu2), N548-8A (pgk1 leu2), N583-2C (gpm1 leu2), and N549-3A (pyk1 leu2).
[c]The activities of the transformants are averages for many different isolates. The numbers in parentheses represent the numbers of independent transformants assayed.
[d]The gcr1 leu2 mutant strain is N525-2C.

In order to demonstrate that the hyperproduction of glycolytic enzymes was specific to the mutational defect complemented by the particular plasmid, assays for ten different glycolytic proteins were conducted on the various transformants. The following Table 3 reports the results for one transformant for each of the six different glycolysis genes which were examined in detail.

TABLE 3

RELATIVE ENZYME ACTIVITIES OF WILD-TYPE AND TRANSFORMED STRAINS

| Strains | GLYCOLYTIC ENZYMES | | | | | | | | | |
| --- | --- | --- | --- | --- | --- | --- | --- | --- | --- | --- |
| | GLK | PGI | PFK | FBA | TPI | GLD | PGK | GPM | ENO | PYK |
| N501-1B | 1.00 | 1.00 | 1.00 | 1.00 | 1.00 | 1.00 | 1.00 | 1.00 | 1.00 | 1.00 |
| Transformant GCR-8 | 1.05 | 0.63 | 1.44 | 0.79 | 0.62 | 0.63 | 0.75 | 0.56 | 0.51 | 1.36 |
| Transformant PGI-19 | 0.64 | 5.63 | 1.26 | 0.57 | 0.58 | 0.75 | 0.51 | 0.32 | 0.54 | 0.82 |
| Transformant TPI-10 | 0.99 | 0.77 | 1.35 | 0.99 | 13.85 | 0.87 | 0.64 | 1.01 | 0.64 | 1.14 |
| Transformant PGK-2 | 0.54 | 0.45 | 1.05 | 0.54 | 0.46 | 0.63 | 2.99 | 0.24 | 0.43 | 0.83 |

TABLE 3-continued

RELATIVE ENZYME ACTIVITIES OF WILD-TYPE AND TRANSFORMED STRAINS

| Strains | GLYCOLYTIC ENZYMES | | | | | | | | | |
|---|---|---|---|---|---|---|---|---|---|---|
| | GLK | PGI | PFK | FBA | TPI | GLD | PGK | GPM | ENO | PYK |
| Transformant GPM-2 | 0.97 | 0.82 | 1.69 | 1.02 | 1.02 | 0.85 | 0.97 | 12.75 | 0.72 | 2.00 |
| Transformant PYK-1 | 1.02 | 0.83 | 1.09 | 0.89 | 1.22 | 0.84 | 1.23 | 0.49 | 0.85 | 6.53 |

The GCR-8 transformant gave nearly wild-type levels of all ten enzymes, while PGI-19, TPI-10, PGK-2, GPM-2 and PYK-1 transformants overproduced their respective glycolytic proteins, but not other enzymes.

It was noted that the plasmids readily segregated (typically 5-50% segregation in fully grown cultures even under selective pressure of leucine prototrophy, so the assayed cultures probably contain cells with a range of number of plasmids. By complementation in E. coli and/or sequencing, TPI1 and PYK1 have both been shown to be the structural gene.

Exploitation of the promoter for TPI1 for the production of human $\alpha_1$-antitrypsin was demonstrated as follows. The plasmid CV13 was employed. CV13 can be maintained by selection of yeast with an average of about ten copies per cell. CV13 is comprised of pBR322, the replicon for the 2$\mu$-plasmid and the yeast LEU2 gene. TPI1 promoter fragment was obtained by cutting the TPI1 gene at the unique KpnI site (bases 511 to 518); and the resulting linearized DNA was then treated with Ba131 for four to five minutes in order to remove the TPI1 structural sequences. Linkers, either EcoRI, Hind III or BamHI, were then inserted. The linkers will then cleave with the appropriate restriction enzyme to provide cohesive ends for insertion of human $\alpha_1$-antitrypsin genes. The human $\alpha_1$-antitrypsin gene was digested with BamHI, which cleaves at the 5'-terminus of the coding strand to remove the information for a single glutamic acid codon from the mature protein. Four different constructions were prepared, as set forth in the following Table 4. From this table it is noted that the glutamic acid codon is substituted by the codons for alanine and proline in three of the constructions having the initiator methionine.

After ligation of the human $\alpha_1$-AT construction into the CV13 plasmid, the resulting plasmid was transformed into S. c. N501-1B. The resulting yeast cells were then grown on a minimal synthetic medium.

TABLE 4

| Plasmid | N-terminal amino acid | Orientation in CV13 |
|---|---|---|
| CAT1 | met glu + hAT* | clockwise |
| C-T$\alpha$2 | met ala pro + hAT | counterclockwise |
| C-T$\alpha$1 | met ala pro + hAT | clockwise |
| C-TS$\alpha$2 | met ala pro + hAT, but missing part of TPI promoter | counterclockwise |

*remainder of approximately 400 amino acids of human $\alpha_1$-antitrypsin

Yeast cells containing the human $\alpha_1$-AT genes were broken open by vortexing with glass beads (0.45 mm) at high speed for 2-3 minutes. The extraction buffer contained 50 mM K$_2$HPO$_4$, 2 mM EDTA, 2 mM 2-mercaptoethanol and 1 mM PMSF (pH7.4) cell debris was removed by centrifugation and the extracts contain 3-4 mg/ml protein as determined by Lowry assays.

The presence of human $\alpha_1$-antitrypsin was determined using a RIA, employing tritium-labeled human $\alpha_1$-AT and antibody directed against the protein. The following Table 5 indicates the results.

TABLE 5

Competition assay for alpha-1 antitrypsin

| Plasmid | Tritium Counts | Average Count | $\alpha_1$-AT [$\mu$g] | Total Protein ($\mu$g) | % Total Protein |
|---|---|---|---|---|---|
| CAT1 | 46010 52257 | 49133.5 | 0.75 | 420 | .18 |
| C-T$\alpha$2 | 12268 13330 | 12799 | 3.35 | 380 | .88 |
| C-T$\alpha$1 | 41635 39071 | 40353 | 0.95 | 360 | .26 |
| C-TS$\alpha$2 | 66490 70038 | 68264 | 0 | 345 | 0 |

| Controls** | Counts |
|---|---|
| 0 $\mu$g $\alpha$-1 | 68440 |
| 0.25 $\mu$g $\alpha$-1 | 65333 |
| 0.5 $\mu$g $\alpha$-1 | 58928 |
| 1.0 $\mu$g $\alpha$-1 | 38468 |
| 2.0 $\mu$g $\alpha$-1 | 19559 |
| 3.0 $\mu$g $\alpha$-1 | 14432 |
| 4.0 $\mu$g $\alpha$-1 | 11155 |
| 5.0 $\mu$g $\alpha$-1 | 9615 |

*Plasmids were grown in yeast strain, N501-1B. 100 $\mu$l of extracts were assayed.
**Non-radioactive alpha-1 antitrypsin mixed with 100 $\mu$l of yeast extract (330 $\mu$g protein)

It is evident from the above results that an immunologically active product is obtained, which is capable of competing with naturally occurring human $\alpha_1$-AT for antibodies to the native protein. Furthermore, the expression of the $\alpha_1$-AT gene is regulated by the TPI promoter, for as is seen, where a portion of the TPI promoter is removed, no $\alpha_1$-AT is produced. In addition, the production of the mammalian protein human $\alpha_1$-AT has not been optimized in the above study, so that the results indicate a minimum production of product which can be further enhanced. Thus, the TPI promoter is found to be an effective promoter for efficiently producing high yields of expression products of alien DNA.

It is evident from the above results that yeast promoters can be efficiently used for the production of foreign proteins by regulating the expression of alien DNA in yeast. The promoters are found to be strong promoters, so as to provide for a high degree of expression. Furthermore, it would appear that the messengers are sufficiently stable as to allow for a significant degree of translation into the desired expression product. Furthermore, by employing the glycolytic promoters and appropriate nutrient media, the expression of the alien DNA can be modulated. In this way, production of the alien DNA can be turned on and off. Thus, the subject invention provides a method for using yeast as efficient host in the production of foreign proteins, where the production may be modulated. In addition, by using the glycolytic regulation gene, one can turn on and off a plurality of glycolytic promoters.

Although the foregoing invention has been described in some detail by way of illustration and example for purposes of clarity of understanding, it will be obvious that certain changes and modification may be practiced within the scope of the appended claims.

What is claimed is:

1. An unglycosylated mature human alpha-1-antitrypsin produced by culturing a yeast cell having an extrachromosomal element capable of replication in *Saccharomyces cerevisiae* and containing a *Saccharomyces cerevisiae* promoter which regulates the transcription of a glycolytic protein, which protein is triose phosphate isomerase, pyruvate kinase, phosphoglucose isomerase, phosphoglycerate mutase, hexokinase 1, hexokinase 2, glucokinase, phosphofructokinase, aldolase or glycolytic regulation protein, said *Saccharomyces cerevisiae* promoter followed downstream by a gene, under the regulation of said promoter, expressing human alpha-1-antitrypsin.

2. An unglycosylated mature human alpha-1-antitrypsin produced by culturing a yeast cell containing an portion integrated into said yeast cell genome, wherein said portion includes a yeast promoter which regulates the transcription of a glycolytic protein, which protein is triose phosphate isomerase; pyruvate kinase, phosphoglucose isomerase, phosphoglycerate mutase, hexokinase 1, hexokinase 2, glucokinase, phosphofructokinase, aldolase, or glycolytic regulation protein, and a gene under the transcription regulation of said promoter and expressing unglycosylated human alpha-1-antitrypsin.

3. An unglycosylated human alpha-1-antitrypsin according to claim 1 or 2 consisting essentially of an N-terminal methionine residue followed by the amino acid sequence shown in the FIG. 1 from amino acid 1 (Glu) to amino acid 394 (Lys).

4. Unglycosylated mature human alpha-1-antitrypsin.

5. The unglycosylated human alpha-1-antitrypsin of claim 4 wherein said alpha-1-antitrypsin consists essentially of an N-terminal methionine residue followed by the amino acid sequence shown in the FIG. 1 from amino acid 1 (Glu) to amino acid 394 (Lys).

6. Mature human alpha-1-antitrypsin produced cytoplasmically in yeast as a mature protein, said protein being unglycosylated and having an amino terminal methionine residue said alpha-1-antitrypsin having the biological activity of the glycosylated form of human alpha-1-antitrypsin.

* * * * *

UNITED STATES PATENT AND TRADEMARK OFFICE
CERTIFICATE OF CORRECTION

PATENT NO. : 5,218,091
DATED     : June 8, 1993
INVENTOR(S) : Glenn H. Kawasaki

It is certified that error appears in the above-indentified patent and that said Letters Patent is hereby corrected as shown below:

In column 15, claim 2, line 17, please delete "portion" and substitute therefor --extrachromosomal element--.

In column 15, claim 2, line 18, please delete "portion" and substitute therefor --extrachromosomal element--.

Signed and Sealed this

Twenty-ninth Day of March, 1994

Attest:

BRUCE LEHMAN

Attesting Officer    Commissioner of Patents and Trademarks